United States Patent
Bartels et al.

(10) Patent No.: US 9,115,130 B2
(45) Date of Patent: Aug. 25, 2015

(54) PROCESS FOR THE PREPARATION OF 2-PHENYL-[1,2,4]TRIAZOLO[1,5-A]PYRIDINE DERIVATIVES

(71) Applicant: Hoffmann-La Roche Inc., Little Falls, NJ (US)

(72) Inventors: Bjoern Bartels, Schopfheim (DE); Serena Maria Fantasia, Basel (CH); Alexander Flohr, Loerrach (DE); Kurt Puentener, Basel (CH); Shaoning Wang, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/455,773

(22) Filed: Aug. 8, 2014

(65) Prior Publication Data

US 2014/0350259 A1    Nov. 27, 2014

Related U.S. Application Data

(63) Continuation of application No. PCT/EP2013/052362, filed on Feb. 7, 2013.

(30) Foreign Application Priority Data

Feb. 9, 2012  (EP) .................................... 12154786

(51) Int. Cl.
C07D 498/02    (2006.01)
C07D 471/04    (2006.01)

(52) U.S. Cl.
CPC .................................... *C07D 471/04* (2013.01)

(58) Field of Classification Search
None
See application file for complete search history.

(56) References Cited

FOREIGN PATENT DOCUMENTS

JP    2011032225 A    2/2011
WO    2012/076430 A1    6/2012

OTHER PUBLICATIONS

Ueda, S. and Nagasawa, H., J. Amer. Chem. Soc. 2009, vol. 131, pp. 15080-15081.*
Chemical Abstracts Record associated with Japanese Published Application No. 2011 032225A.
ISR of WO 2013/117610.
Thomson Innovation record and translation of Japanese Published Application No. 2011 032225A.
Ueda and Nagasawa, "Facile synthesis of 1,2,4-triazoles via a copper-catalyzed tandem addition-oxidative cyclization" J Am Chem Soc. 131(42):15080-1 (2009).
Written Opinion of WO 2013/117610.

* cited by examiner

*Primary Examiner* — Heidi Reese
(74) *Attorney, Agent, or Firm* — Mark D. Kafka

(57) ABSTRACT

The invention relates to a novel process for the preparation of 2-phenyl-[1,2,4]triazolo[1,5-a]pyridine derivatives of formula I or of a salt thereof

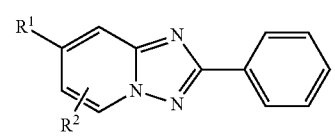

I wherein
$R^1$ stands for hydrogen, a halogen, for an optionally protected hydroxyl group or for an optionally protected amino group and
$R^2$ is hydrogen or a halogen.
2-Phenyl-[1,2,4]triazolo[1,5-a]pyridine derivatives of formula I with their 1,2,4-triazole nucleus build the structural core of a great number of functionalized molecules in medicinal chemistry.

13 Claims, No Drawings

PROCESS FOR THE PREPARATION OF 2-PHENYL-[1,2,4]TRIAZOLO[1,5-A]PYRIDINE DERIVATIVES

This application is a continuation of International Application No. PCT/EP2013/052362, filed Feb. 7, 2013, which claims the benefit of European Application No. 12154786.3, filed Feb. 9, 2012, each of which is incorporated herein by reference in its entirety.

The invention relates to a novel process for the preparation of 2-phenyl-[1,2,4]triazolo[1,5-a]pyridine derivatives of formula I or of a salt thereof

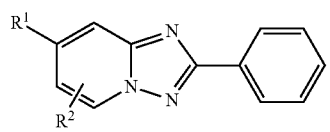

wherein
$R^1$ stands for hydrogen, a halogen, for an optionally protected hydroxyl group or for an optionally protected amino group and
$R^2$ is hydrogen or a halogen.

2-Phenyl-[1,2,4]triazolo[1,5-a]pyridine derivatives of formula I with their 1,2,4-triazole nucleus build the structural core of a great number of functionalized molecules in medicinal chemistry (J. Am. Chem. Soc. 2009, 131, 15080-15081).

A number of attempts have been described to practically synthesize these important molecules.

A quite advanced approach has been described by Nagasawa et al. in J. Am. Chem. Soc. 2009, 131, 15080-15081, which is illustrated with the scheme below.

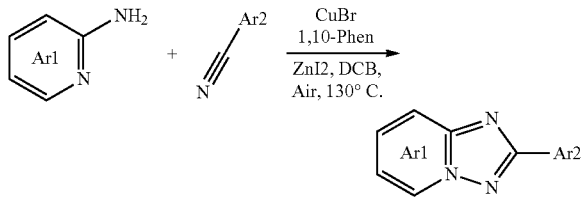

They found that the addition of zinc iodide significantly improved reaction efficacy i.e. doubled the yield of their target product. 1,2-Dichlorobenzene was reported to be the solvent giving the best yields.

However, it was found that this reaction is hardly transferable to large scale. On one hand the use of 1,2-dichlorobenezene—a CFC (chlorofluorocarbon)—as solvent is not desired on industrial scale productions as of its ozone depleting activity. On the other hand it was found that the use of zinc iodide in the synthesis of the 7-bromo derivatives of the 2-phenyl-[1,2,4]triazolo[1,5-a]pyridine derivatives of formula I affords to a large extent the non separable 7-iodo derivative as by product. In addition, tedious chromatographic purifications of the crudes were required to isolate the pure products.

Object of the present invention therefore was to find a synthesis which is applicable on large scale and which is free from the drawbacks encountered in the synthesis known from the state of the art.

The objective could be achieved with the process of the present invention for the preparation of 2-phenyl-[1,2,4]triazolo[1,5-a]pyridine derivatives of formula I or of a salt thereof

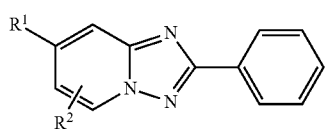

wherein,
$R^1$ stands for hydrogen, a halogen, for an optionally protected hydroxyl group or for an optionally protected amino group and
$R^2$ is hydrogen or a halogen,
the process which comprises the conversion of a pyridine compound of formula II or of a salt thereof,

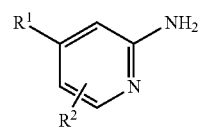

wherein,
$R^1$ and $R^2$ are as above, with benzonitrile in the presence of a Cu-catalyst, a 1,10-phenanthroline derivative and of a mixture $O_2/N_2$, characterized in that no other solvent than the reactant benzonitrile is present in the process.

The following definitions are set forth to illustrate and define the meaning and scope of the various terms used to describe the invention herein.

The term "salt" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid, trifluoroacetic acid and the like. Preferred salts with acids are formates, maleates, citrates, hydrochlorides, hydrobromides and methanesulfonic acid salts, with hydrochlorides and hydrobromides being especially preferred.

The term "protected amino group" refers to an amino group protected with any substituents conventionally used to hinder the reactivity of the amino group. Suitable amino protecting groups are described in Green T., "Protective Groups in Organic Synthesis", $4^{th}$ Ed. by Wiley Interscience, 2007, Chapter 7, 696 ff. Suitable amino protecting groups can be selected from Boc, Fmoc, Cbz, Moz, Troc, Teoc or Voc, more particularly Boc is used.

The term "protected hydroxyl group" refers to a hydroxyl group protected with any substituents conventionally used to hinder the reactivity of the hydroxyl group. Suitable hydroxy protecting groups are described in Green T., "Protective Groups in Organic Synthesis", 4th Ed. by Wiley Interscience, 2007, Chapter 2, 16 ff. Suitably trifluoromethylsulfonyl (Tf), trimethylsilyl (TMS) or benzyl (Bn) is used.

The term halogen refers to chlorine, bromine or iodine.

The pyridine compounds of formula

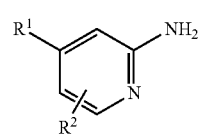

or salts thereof, wherein $R^1$ and $R^2$ are as above are as a rule commercially available compounds, otherwise they are accessible with synthetic methods well known to the skilled in the art.

In a particular embodiment of the present invention $R^1$ stands for a halogen and $R^2$ for hydrogen, more particularly $R^1$ stands for bromine.

The process of the present invention is characterized in that the reactant benzonitrile is the sole solvent and that no additional solvent is used.

The reaction is further characterized in that the reaction temperature is selected between 80° C. and 170° C., in a more particular embodiment between 110° C. and 150° C. and even more particular at about 130° C.

The reaction pressure can be selected between 1 and 100 bar. In a more particular embodiment the pressure is selected between 1 and 60 bar and even more particular between 1 and 20 bar.

It was found that increasing the concentration of the pyridine compound of formula II in benzonitrile positively influences the yield of the target product.

Thus the concentration of the pyridine compound of formula II in benzonitrile can be chosen between 2 wt. % and 30 wt. %.

In a particular embodiment of the present invention the concentration of the pyridine compound of formula II in benzonitrile is between 5 wt. % and 20 wt. %, even more particular between 7 wt. % and 15 wt. %.

The process can be performed with mixtures $O_2/N_2$ having an $O_2$ content of 1 Vol % to 21 Vol % $O_2$. It is hereby understood that the mixtures $O_2/N_2$ as defined before include air.

In a more particular embodiment the $O_2$ content in the mixture $O_2/N_2$ is between 3 Vol % and 8 Vol % $O_2$, even more particular between 5 Vol % and 8 Vol % $O_2$.

The process of the present invention is characterized in that a Cu-catalyst is present.

As a rule CuBr is selected in case $R^1$ in the pyridine compound of formula II stands for bromine, for an optionally protected hydroxyl group or for an optionally protected amino group.

CuBr is also selected in case $R^1$ in the pyridine compound of formula II stands for hydrogen and $R^2$ for bromine or hydrogen.

CuCl is selected in case $R^1$ in the pyridine compound of formula II stands for chlorine and CuI is selected in case $R^1$ in the pyridine compound of formula II stands for iodine.

In the particular embodiment of the invention mentioned above, wherein $R^1$ in the pyridine compound of formula II stands for bromine the Cu-catalyst is CuBr.

The Cu-catalyst is as a rule applied in amounts of 0.1 mol % to 20 mol %, more particularly in amounts of 1 mol % to 5 mol % related to the pyridine compound of formula II.

The process of the present invention is further characterized in that a 1,10 phenanthroline derivative is present. As a rule the commercially available monohydrate of 1,10 phenanthroline is used.

The 1,10 phenanthroline derivative is as a rule applied in amounts of 0.1 mol % to 20 mol %, more particularly in amounts of 1 mol % to 5 mol % related to the pyridine compound of formula II.

While it is well understood by the skilled in the art that reaction time can vary with the reaction parameters selected, as a rule the reaction is completed after about 20 h to 30 h.

Isolation of the desired 2-phenyl-[1,2,4]triazolo[1,5-a]pyridine derivative of formula I from the reaction mixture can as a rule happen by filtration. Further purification of the crude product may happen by charcoal treatment of a solution of the product e.g. in a suitable solvent like ethylacetate and by subsequent crystallization.

EXAMPLES

Abbreviations:
r.t.=room temperature, DCM=dichloromethane, THF=tetrahydrofuran, TBME=tert.-butyl methyl ether, EtOAc=ethyl acetate, NCMe=acetonitrile.

Comparative Example 1

With $ZnI_2$, But No Additional Solvent

7-Bromo-2-phenyl-[1,2,4]triazolo[1,5-a]pyridine

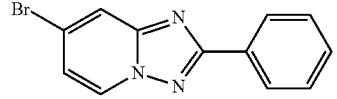

A mixture of 2-amino-4-bromopyridine (5.00 g, 28.9 mmol), copper (I) bromide (207 mg, 1.44 mmol), 1,10-phenanthroline monohydrate (289 mg, 1.44 mmol), zinc iodide (923 mg, 2.89 mmol) and benzonitrile (125 mL) was heated in a 250-mL 3-necked flask to 130° C. During 23 h a gentle flow of air was bubbled through the reaction mixture (93% conversion, HPLC method cf. example 1.3). The dark brown suspension was then cooled to 0-5° C. and filtered. The filter cake was washed with TBME (50 mL) and dried to yield crude 7-bromo-2-phenyl-[1,2,4]triazolo[1,5-a]pyrdine (5.36 g, 51%) as a green solid with 76.0% purity (HPLC area-%, HPLC method cf. example 1.3). Major by-product: 7-Iodo-2-phenyl-[1,2,4]triazolo[1,5-a]pyridine (13.0%).

Charcoal treatment of the crude product with Norit SA II (1.1 g) in EtOAc (200 mL) at reflux and subsequent crystallization (via partial evaporation of EtOAc) afforded 7-bromo-2-phenyl-[1,2,4]triazolo[1,5-a]pyridine (3.71 g, 40%) as a white solid with 90.4% purity (HPLC area-%, HPLC method see below) containing as a non-separable impurity 8.6% of 7-iodo-2-phenyl-[1,2,4]triazolo[1,5-a]pyridine (HPLC method: X-Bridge Phenyl column, 50×4.6 mm; mobile phase, A: water/NCMe (95:5), B: NCMe, C: gylcine buffer pH 9; flow: 2.5 ml/min; gradient from 90/5/5 (A/B/C) to 10/85/5 (A/B/C) within 4 min, isocratic 10/85/5 (A/B/C) for 1 min. Retention time: 1.37 min (2-amino-4-bromopyridine), 2.54 min (7-bromo-2-phenyl-[1,2,4]triazolo[1,5-a]pyridine), 2.67 min (7-iodo-2-phenyl-[1,2,4]triazolo[1,5-a]pyridine)).

Comparative Example 2

According to JACS, 2009, 131, 15080-15081

7-Bromo-2-phenyl-[1,2,4]triazolo[1,5-a]pyridine

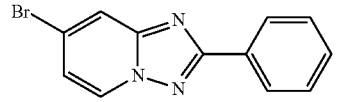 [SMILES: Brc1ccn2nc(-c3ccccc3)nc2c1]

A mixture of 2-amino-4-bromopyridine (0.50 g, 2.89 mmol), copper (I) bromide (20.7 mg, 0.14 mmol), 1,10-phenanthroline monohydrate (28.9 mg, 0.14 mmol), zinc iodide (92.3 mg, 0.29 mmol), benzonitrile (298 mg, 0.29 mL, 2.89 mmol) and 1,2-dichlorobenzene (25 mL) was heated in a 100-mL 3-necked flask to 130° C. During 22 h a gentle flow of air was bubbled through the reaction mixture (69% conversion, HPLC method cf. example 1.3). The dark brown suspension was then cooled to 0-5° C. and filtered. The filter cake was washed with EtOAc (30 mL) and the combined filtrates were concentrated on vacuum such that most EtOAc was evaporated off. The resulting solution of the crude product in 1,2-dichlorobenzene was then loaded on a silica gel column to yield after chromatography (hexane/EtOAC from 9:1 to 7:3) 7-bromo-2-phenyl-[1,2,4]triazolo[1,5-a]pyridine (345 mg, 41%) as an off-white solid with 97.6% purity (HPLC area-%, HPLC method cf. comparative example 1) containing as an non-separable impurity 1.4% of 7-iodo-2-phenyl-[1,2,4]triazolo[1,5-a]pyridine.

Example 1.1

7-Bromo-2-phenyl-[1,2,4]triazolo[1,5-a]pyridine

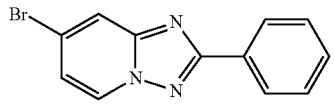 [SMILES: Brc1ccn2nc(-c3ccccc3)nc2c1]

A mixture of 2-amino-4-bromopyridine (10.0 g, 56.6 mmol), copper (I) bromide (400 mg, 2.70 mmol), 1,10-phenanthroline monohydrate (560 mg, 2.80 mmol) and benzonitrile (130 mL) was heated in a 350 mL 4-necked flask to 130° C. During 45 h a gentle flow of $O_2/N_2$ (5:95) was bubbled through the reaction mixture (>99% conversion, HPLC method see below). The dark brown suspension was then cooled to 0-5° C. and filtered. The filter cake was washed with TBME (50 mL) and dried to yield crude 7-bromo-2-phenyl-[1,2,4]triazolo[1,5-a]pyridine (11.6 g, 75%) as a green solid with 100% purity (HPLC area-%, HPLC method see below).

Charcoal treatment of the crude product with Norit SA II (2.5 g) in EtOAc (400 mL) at reflux and subsequent crystallization (via partial evaporation of EtOAc) afforded 7-bromo-2-phenyl-[1,2,4]triazolo[1,5-a]pyridine (9.81 g, 63%) as a white solid with 100% purity (HPLC area-%, HPLC method: Onyx monolithic C18 column, 100×4.6 mm; mobile phase, A: water/NCMe (95:5), B: NCMe; flow: 2 ml/min; gradient from 95/5 (A/B) to 15/85 (A/B) within 3 min, isocratic 15/85 (A/B) for 2.5 min, gradient 15/85 (A/B) to 95/5 (A/B) within 2 min. Retention time: 2.50 min (2-amino-4-bromopyridine), 3.39 min (7-bromo-2-phenyl-[1,2,4]triazolo[1,5-a]pyridine)).

EI-MS: m/z=273.99 $(M+H)^+$.

Example 1.2a-d

7-Bromo-2-phenyl-[1,2,4]triazolo[1,5-a]pyridine

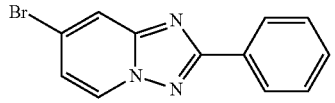

A mixture of 2-amino-4-bromopyridine (1.00 g, 5.66 mmol), copper (I) bromide (41.5 mg, 0.28 mmol), 1,10-phenanthroline monohydrate (56.7 mg, 0.28 mmol) and benzonitrile (13 mL) was heated in a 100-mL 4-necked flask to 110° C. During 23 h a gentle flow of $O_2/N_2$ (5:95) was bubbled through the reaction mixture (>99% conversion, HPLC method cf. example 1.1). The dark brown suspension was then cooled to 0-5° C. and filtered. The filter cake was washed with TBME (50 mL) and dried to yield crude 7-bromo-2-phenyl-[1,2,4]triazolo[1,5-a]pyridine (1.21 g, 79%) as a green solid with 99.0% purity (HPLC area-%, HPLC method cf. example 1.1).

The reactions in Table 1 were performed according to the procedure described above but at elevated reaction temperatures:

TABLE 1

| Example | Reaction Temperature | Conversion after 23 h | Yield | Purity (HPLC area-%) |
| --- | --- | --- | --- | --- |
| 1.2b | 130° C. | 100% | 73% | 100% |
| 1.2c | 150° C. | 77% | 44% | 100% |
| 1.2d | 175° C. | 29% | decomp. | — |

Example 1.3

7-Bromo-2-phenyl-[1,2,4]triazolo[1,5-a]pyridine

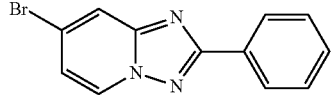

A mixture of 2-amino-4-bromopyridine (5.00 g, 28.9 mmol), copper (I) bromide (207 mg, 1.44 mmol), 1,10-phenanthroline monohydrate (289 mg, 1.44 mmol), and benzonitrile (125 mL) was heated in a 250-mL 3-necked flask to 130° C. During 23 h a gentle flow of air was bubbled through the reaction mixture (80% conversion, HPLC method see below). The dark brown suspension was then cooled to 0-5° C. and filtered. The filter cake was washed with TBME (50 mL) and dried to yield crude 7-bromo-2-phenyl-[1,2,4]triazolo[1,5-a]pyridine (4.87 g, 60%) as a green solid with 97.3% purity (HPLC area-%, HPLC method see below).

Charcoal treatment of the crude product with Norit SA II (1.0 g) in EtOAc (200 mL) at reflux and subsequent crystallization (via partial evaporation of EtOAc) afforded 7-bromo-2-phenyl-[1,2,4]triazolo[1,5-a]pyridine (3.97 g, 50%) as a white solid with 98.9% purity (HPLC area-%, HPLC method: X-Bridge C18 column, 150×4.6 mm; mobile phase, A: water/NCMe (95:5), B: NCMe, C: $NBu_4HSO_4$ buffer pH 3-4; flow: 1.5 ml/min; gradient from 90/0/10 (A/B/C) to 5/85/10 (A/B/C) within 6 min, isocratic 5/85/10 (A/B/C) for 4 min. Retention time: 2.25 min (2-amino-4-bromopyridine), 3.00 min (N-(4-bromo-pyridin-2-yl)-benzamidine), 6.40 min (7-bromo-2-phenyl-[1,2,4]triazolo[1,5-a]pyridine), 6.62 min (7-iodo-2-phenyl-[1,2,4]triazolo[1,5-a]pyridine)).

Example 1.4

7-Bromo-2-phenyl-[1,2,4]triazolo[1,5-a]pyridine

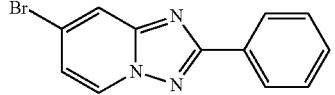

A mixture of 2-amino-4-bromopyridine (5.00 g, 28.9 mmol), copper (I) bromide (207 mg, 1.44 mmol), 1,10-phenanthroline monohydrate (289 mg, 1.44 mmol) and benzonitrile (65 mL) was heated in a 100-mL 4-necked flask to 130° C. During 23 h a gentle flow of air was bubbled through the reaction mixture (>99% conversion, HPLC method cf. example 1.3). The dark brown suspension was then cooled to 0-5° C. and filtered. The filter cake was washed with TBME (50 mL) and dried to yield crude 7-bromo-2-phenyl-[1,2,4]triazolo[1,5-a]pyridine (6.13 g, 75%) as a green solid with 97.1% purity (HPLC area-%, HPLC method cf. example 1.3).

Charcoal treatment of the crude product with Norit SA II (1.2 g) in EtOAc (220 mL) at reflux and subsequent crystallization (via partial evaporation of EtOAc) afforded 7-bromo-2-phenyl-[1,2,4]triazolo[1,5-a]pyridine (5.23 g, 65%) as a white solid with 98.8% purity (HPLC area-%, HPLC method cf. example 1.3).

Example 1.5

7-Bromo-2-phenyl-[1,2,4]triazolo[1,5-a]pyridine

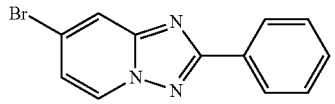 [SMILES: Brc1ccn2nc(-c3ccccc3)nc2c1]

A mixture of 2-amino-4-bromopyridine (5.00 g, 28.9 mmol), copper (I) bromide (207 mg, 1.44 mmol), 1,10-phenanthroline monohydrate (289 mg, 1.44 mmol) and benzonitrile (40 mL) was heated in a 100-mL 4-necked flask to 130° C. During 23 h a gentle flow of air was bubbled through the reaction mixture (91% conversion, HPLC method cf. example 1.3). The dark brown suspension was then cooled to 0-5° C. and filtered. The filter cake was washed with TBME (50 mL) and dried to yield crude 7-bromo-2-phenyl-[1,2,4]triazolo[1,5-a]pyridine (6.39 g, 72%) as a green solid with 89.4% purity (HPLC area-%, HPLC method cf. example 1.3).

Example 1.6

7-Bromo-2-phenyl-[1,2,4]triazolo[1,5-a]pyridine

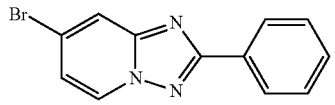

A mixture of 2-amino-4-bromopyridine (5.00 g, 28.3 mmol), copper (I) bromide (207 mg, 1.44 mmol), 1,10-phenanthroline monohydrate (284 mg, 1.44 mmol) and benzonitrile (60 mL) was heated in a 380-mL autoclave to 130° C. and stirred for 23 h under 20 bar of $O_2/N_2$ (5:95). After the autoclave was vented and opened (100% conversion, HPLC method cf. example 1.3), the dark brown reaction suspension was then cooled to 0-5° C. and filtered. The filter cake was washed with TBME (40 mL) and dried to yield crude 7-bromo-2-phenyl-[1,2,4]triazolo[1,5-a]pyridine (5.12 g, 64%) as a green solid with 97.0% purity (HPLC area-%, HPLC method see example 1.3).

Charcoal treatment of the crude product with Norit SA II (1.0 g) in EtOAc (200 mL) at reflux and subsequent crystallization (via partial evaporation of EtOAc) afforded 7-bromo-2-phenyl-[1,2,4]triazolo[1,5-a]pyridine (4.18 g, 53%) as a white solid with 99.2% purity (HPLC area-%, HPLC method cf. example 1.3).

Example 1.7

7-Bromo-2-phenyl-[1,2,4]triazolo[1,5-a]pyridine

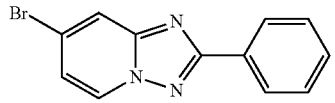

A mixture of 2-amino-4-bromopyridine (5.00 g, 28.3 mmol), copper (I) bromide (207 mg, 1.44 mmol), 1,10-phenanthroline monohydrate (284 mg, 1.44 mmol) and benzonitrile (125 mL) was heated in a 380-mL autoclave to 130° C. and stirred for 23 h under 20 bar of air. After the autoclave was vented and opened (100% conversion, HPLC method cf. example 1.3), the dark brown reaction suspension was then cooled to 0-5° C. and filtered. The filter cake was washed with TBME (40 mL) and dried to yield crude 7-bromo-2-phenyl-[1,2,4]triazolo[1,5-a]pyridine (4.74 g, 60%) as a green solid with 97.7% purity (HPLC area-%, HPLC method cf. example 1.3).

Charcoal treatment of the crude product with Norit SA II (0.9 g) in EtOAc (200 mL) at reflux and subsequent crystallization (via partial evaporation of EtOAc) afforded 7-bromo-2-phenyl-[1,2,4]triazolo[1,5-a]pyridine (3.76 g, 48%) as a white solid with 99.4% purity (HPLC area-%, method cf. example 1.3).

Example 1.8

7-Bromo-2-phenyl-[1,2,4]triazolo[1,5-a]pyridine

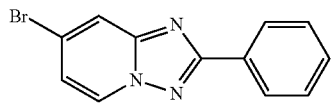

A mixture of 2-amino-4-bromopyridine (5.00 g, 28.3 mmol), copper (I) bromide (207 mg, 1.44 mmol), 1,10-phenanthroline monohydrate (284 mg, 1.44 mmol) and benzonitrile (60 mL) was heated in a 380-mL autoclave to 130° C. and stirred for 23 h under 60 bar of $O_2/N_2$ (5:95). After the autoclave was vented and opened (100% conversion, GC method see below), the dark brown reaction suspension was then cooled to 0-5° C. and filtered. The filter cake was washed with TBME (40 mL) and dried to yield crude 7-bromo-2-phenyl-[1,2,4]triazolo[1,5-a]pyridine (5.71 g, 74%) as a green solid with 100% purity (GC area-%, GC method: column J&W 113-5432 SE-54 (30 m, ID 0.32 mm), oven 80° C. to 140° C. (5° C./min plus 5 min hold) then to 280° C. (10° C./min & 5 min hold), injector 250° C., detector 300° C., carrier gas $H_2$ (66 kPa), split ratio 1/20. Sample preparation: 1-1.5 mg of the sample were dissolved in 1 ml methanol, 2 µl were injected. Retention times: 10.4 min (2-amino-4-bromopyridine), 12.1 min (benzamide), 26.9 (3,5-diphenyl-1,2,4-oxadiazol), 29.8 min (7-bromo-2-phenyl-[1,2,4]triazolo[1,5-a]pyridine)).

Example 1.9

7-Bromo-2-phenyl-[1,2,4]triazolo[1,5-a]pyridine

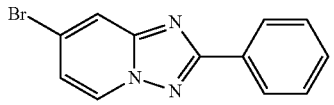 [SMILES: Brc1ccn2nc(-c3ccccc3)nc2c1]

A mixture of 2-amino-4-bromopyridine (100.0 g, 0.566 mol), copper (I) bromide (4.15 g, 28.3 mmol), 1,10-phenanthroline monohydrate (5.67 g, 28.3 mmol) and benzonitrile (600 mL) was heated in a 1.5-L autoclave to 130° C. and stirred for 23 h under a continuous gas flow ($O_2/N_2$ 8:92) of 200 mL/min (constant pressure: 20 bar). After the autoclave was vented and opened (100% conversion, GC method cf. example 1.8), the dark brown reaction suspension was cooled to 0-5° C. and filtered. The filter cake was washed with MeOH (600 mL) and dried to yield crude 7-bromo-2-phenyl-[1,2,4]triazolo[1,5-a]pyridine (120.6 g, 78%) as a green solid with 100% purity (HPLC area-%, GC method cf. example 1.8).

Example 2

7-Iodo-2-phenyl-[1,2,4]triazolo[1,5-a]pyridine

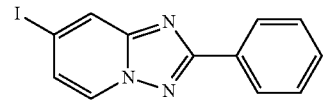 [SMILES: Ic1ccn2nc(-c3ccccc3)nc2c1]

A mixture of 2-amino-4-iodopyridine (2.60 g, 11.8 mmol), copper (I) iodide (115 mg, 0.60 mmol), 1,10-phenanthroline monohydrate (120 mg, 0.60 mmol) and benzonitrile (33 mL) was heated in a 100 mL 4-necked flask to 130° C. During 23 h a gentle flow of $O_2/N_2$ (5:95) was bubbled through the reaction mixture (99% conversion, HPLC method see below). The dark brown suspension was then cooled to 0-5° C. and filtered. The filter cake was washed with TBME (10 mL) and dried to yield crude 7-iodo-2-phenyl-[1,2,4]triazolo[1,5-a]pyridine (2.31 g, 61%) as a green solid with 100% purity (HPLC area-%, HPLC method see below).

Charcoal treatment of the crude product with Norit SA II (0.6 g) in EtOAc (100 mL) at reflux and subsequent crystallization (via partial evaporation of EtOAc) afforded 7-iodo-2-phenyl-[1,2,4]triazolo[1,5-a]pyridine (1.82 g, 48%) as a white solid with 100% purity (HPLC area-%, method: Onyx Monolithic C18 column, 100×4.6 mm; mobile phase, A: water/NCMe (95:5), B: NCMe; flow: 2 ml/min; gradient from 95/5 (A/B) to 15/85 (A/B) within 3 min, isocratic 15/85 (A/B) for 2.5 min, gradient 15/85 (A/B) to 95/5 (A/B) within 2 min. Retention time: 2.77 min(2-amino-4-iodopyridine), 3.51 min (7-iodo-2-phenyl-[1,2,4]triazolo[1,5-a]pyridine)).

EI-MS: m/z=321.98 (M+H)$^+$.

Example 3

7-Amino-2-phenyl-[1,2,4]triazolo[1,5-a]pyridine

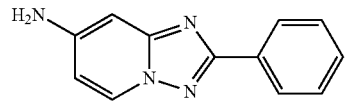 [SMILES: Nc1ccn2nc(-c3ccccc3)nc2c1]

A mixture of 2,4-diamino-pyridine (1.26 g, 11.5 mmol), copper (I) bromide (82.8 mg, 0.57 mmol), 1,10-phenanthroline monohydrate (114.0 mg, 0.57 mmol) and benzonitrile (13 mL) was heated in a 50 mL 3-necked flask to 150° C. During 41 h a gentle flow of $O_2/N_2$ (5:95) was bubbled through the reaction mixture (conversion 42%, HPLC method see below). The reaction mixture was then filtered. The resulting clear brown solution was evaporated to dryness and the crude was product purified by silica gel chromatography (hexane/EtOAc 2:8) to yield 7-amino-2-phenyl-[1,2,4]triazolo[1,5-a]pyridine (0.72 g, 29%) as a light yellow solid with 99.0% purity (HPLC area-%, HPLC method: X-Bridge C18 column, 150×4.6 mm; mobile phase, A: water/NCMe (95:5), B: NCMe, C: $NBu_4HSO_4$ buffer pH 3-4; flow: 1.5 ml/min; gradient from 90/0/10 (A/B/C) to 5/85/10 (A/B/C) within 6 min, isocratic 5/85/10 (A/B/C) for 4 min. Retention time: 0.95 min (2,4-diamino-pyridine), 4.08 min (7-amino-2-phenyl-[1,2,4]triazolo[1,5-a]pyridine)).

EI-MS: m/z=211.09 (M+H)$^+$.

Example 4

7-Chloro-2-phenyl-[1,2,4]triazolo[1,5-a]pyridine

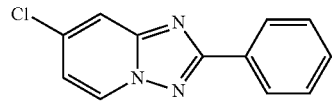 [SMILES: Clc1ccn2nc(-c3ccccc3)nc2c1]

A mixture of 2-amino-4-chloropyridine (5.00 g, 38.9 mmol), copper (I) chloride (195 mg, 1.97 mmol), 1,10-phenanthroline monohydrate (390 mg, 1.97 mmol) and benzonitrile (65 mL) was heated in a 100 mL 4-necked flask to 130° C. During 23 h a gentle flow of $O_2/N_2$ (5:95) was bubbled through the reaction mixture (>99% conversion, HPLC method see below). The dark brown suspension was then cooled to 0-5° C. and filtered. The filter cake was washed with TBME (50 mL) and dried to yield crude 7-chloro-2-phenyl-[1,2,4]triazolo[1,5-a]pyridine (7.09 g, 79%) as a green solid with 100% purity (HPLC area-%, method see below).

Charcoal treatment of the crude product with Norit SA II (1.50 g) in EtOAc (240 mL) at reflux and subsequent crystallization (via partial evaporation of EtOAc) afforded 7-chloro-2-phenyl-[1,2,4]triazolo[1,5-a]pyridine (6.25 g, 70%) as a white solid with 100% purity (HPLC area-%, method: Onyx Monolithic C18 column, 100×4.6 mm; mobile phase, A: water with 5% NCME, B: NCMe; flow: 2 ml/min; gradient from 95/5 (A/B) to 15/85 (A/B) within 3 min, isocratic 15/85 (A/B) for 2.5 min, gradient 15/85 (A/B) to 95/5 (A/B) within 2 min. Retention time: 2.53 min(2-amino-4-chloropyridine), 3.31 min (7-chloro-2-phenyl-[1,2,4]triazolo[1,5-a]pyridine)).

ELMS: m/z=230.3 (M+H)$^+$.

Example 5

8-Bromo-2-phenyl-[1,2,4]triazolo[1,5-a]pyridine

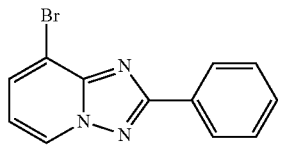 [SMILES: Brc1cccn2nc(-c3ccccc3)nc12]

A mixture of 2-amino-3-bromopyridine (2.00 g, 11.2 mmol), copper (I) bromide (240 mg, 1.64 mmol), 1,10-phenanthroline monohydrate (336 mg, 1.68 mmol) and benzonitrile (25 mL) was heated in a 50-mL 3-necked flask to 130° C. During 4 d a gentle flow of ($O_2/N_2$ 5:95) was bubbled through the reaction mixture (>99% conversion, HPLC method see below). The dark brown suspension was then cooled to 0-5° C. and filtered. The filter cake was washed with TBME (10 mL) and dried to yield crude 8-bromo-2-phenyl-[1,2,4]triazolo[1,5-a]pyridine (1.85 g, 60%) as a light brown solid with 97.5% purity (HPLC area-%, HPLC method see below).

Charcoal treatment of the crude product with Norit SA II (0.4 g) in EtOAc (65 mL) at reflux and subsequent crystallization (via partial evaporation of EtOAc) afforded 8-bromo-2-phenyl-[1,2,4]triazolo[1,5-a]pyridine (1.07 g, 35%) as an off-white solid with >99.9% purity (HPLC area-%, HPLC method: Onyx monolithic C18 column, 100×4.6 mm; mobile phase, A: water/NCMe (95:5), B: NCMe; flow: 2.0 ml/min; gradient from 95/5 (A/B) to 15/85 (A/B) within 3 min, isocratic 15/85 (A/B) for 2.5 min. Retention time: 2.34 min (2-amino-3-bromopyridine), 3.32 min (8-bromo-2-phenyl-[1,2,4]triazolo[1,5-a]pyridine).

EI-MS: m/z=274.00 $(M+H)^+$.

Example 6

6-Bromo-2-phenyl-[1,2,4]triazolo[1,5-a]pyridine

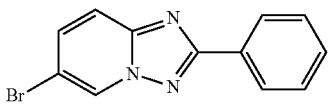 [SMILES: Brc1ccc2nc(-c3ccccc3)nn2c1]

A mixture of 2-amino-5-bromopyridine (2.00 g, 11.6 mmol), copper (I) bromide (160 mg, 1.09 mmol), 1,10-phenanthroline monohydrate (225 mg, 1.12 mmol) and benzonitrile (25 mL) was heated in a 50-mL 3-necked flask to 130° C. During 24 h a gentle flow of ($O_2/N_2$ 5:95) was bubbled through the reaction mixture (>97% conversion, HPLC method see below). The dark brown suspension was then cooled to 0-5° C. and filtered. The filter cake was washed with TBME (10 mL) and dried to yield crude 6-bromo-2-phenyl-[1,2,4]triazolo[1,5-a]pyridine (1.14 g, 36%) as a light brown solid with 99.7% purity (HPLC area-%, HPLC method see below).

Charcoal treatment of the crude product with Norit SA II (0.25 g) in EtOAc (40 mL) at reflux and subsequent crystallization (via partial evaporation of EtOAc) afforded 6-bromo-2-phenyl-[1,2,4]triazolo[1,5-a]pyridine (0.83 g, 26%) as a white solid with >99.9% purity (HPLC area-%, HPLC method: Onyx monolithic C18 column, 100×4.6 mm; mobile phase, A: water/NCMe (95:5), B: NCMe; flow: 2.0 ml/min; gradient from 95/5 (A/B) to 15/85 (A/B) within 3 min, isocratic 15/85 (A/B) for 2.5 min. Retention time: 2.34 min (2-amino-5-bromopyridine), 3.45 min (6-bromo-2-phenyl-[1,2,4]triazolo[1,5-a]pyridine)).

EI-MS: m/z=274.00 $(M+H)^+$.

Example 7

2-Phenyl-[1,2,4]triazolo[1,5-a]pyridine

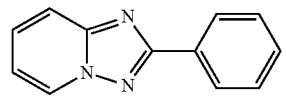

A mixture of 2-amino-pyridine (2.00 g, 21.0 mmol), copper (I) bromide (160 mg, 1.09 mmol), 1,10-phenanthroline monohydrate (225 mg, 1.12 mmol) and benzonitrile (25 mL) was heated in a 50-mL 3-necked flask to 130° C. During 27 h a gentle flow of ($O_2/N_2$ 5:95) was bubbled through the reaction mixture (>99% conversion, HPLC method see below). The dark brown suspension was then cooled to 0-5° C. and filtered. The filtrate was evaporated at 60° C./0.1 mbar to dryness and the dark brown residue dissolved in DCM (30 mL). The organic solution was washed with water (30 mL), dried over sodium sulphate, filtered and evaporated to yield 6.07 g of crude 2-phenyl-[1,2,4]triazolo[1,5-a]pyridine containing approx. 4 g of residual benzonitrile.

Charcoal treatment of the crude product with Norit SA II (0.90 g) in EtOAc (140 mL) at reflux and subsequent crystallization (via partial evaporation of EtOAc and addition of heptane) afforded 2-phenyl-[1,2,4]triazolo[1,5-a]pyridine (2.00 g, 48%) as a yellowish solid with >99.9% purity (HPLC area-%, HPLC method: Onyx monolithic C18 column, 100×4.6 mm; mobile phase, A: water/NCMe (95:5), B: NCMe; flow: 2.0 ml/min; gradient from 95/5 (A/B) to 15/85 (A/B) within 3 min, isocratic 15/85 (A/B) for 2.5 min. Retention time: 1.63 min (2-amino-pyridine), 2.85 min (2-phenyl-[1,2,4]triazolo[1,5-a]pyridine)).

EI-MS: m/z=196.09 $(M+H)^+$.

Example 8

7-Benzyloxy-2-phenyl-[1,2,4]triazolo[1,5-a]pyridine

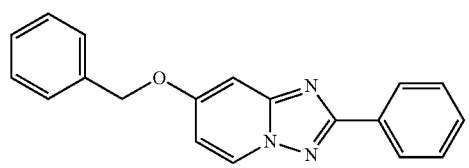 [SMILES: c1ccc(COc2ccn3nc(-c4ccccc4)nc3c2)cc1]

A mixture of 2-amino-4-benzyloxypyridine (2.00 g, 9.49 mmol), copper (I) bromide (70 mg, 0.05 mmol), 1,10-phenanthroline monohydrate (95 mg, 0.05 mmol) and benzonitrile (25 mL) was heated in a 50-mL 3-necked flask to 130° C. During 23 h a gentle flow of ($O_2/N_2$ 5:95) was bubbled through the reaction mixture (>99% conversion, HPLC method see below). The dark brown solution was then evaporated at 60° C./0.1 mbar to dryness and the dark brown residue dissolved in DCM (30 mL). The organic solution was washed with water (30 mL), dried over sodium sulphate, filtered and evaporated to yield an dark oil containing crude 7-benzyloxy-2-phenyl-[1,2,4]triazolo[1,5-a]pyridine and residual benzonitrile.

Charcoal treatment of the crude product with Norit SA II (0.90 g) in EtOAc (120 mL) at reflux, filtration and subsequent crystallization (via partial evaporation of EtOAc and addition of heptane) afforded 7-benzyloxy-2-phenyl-[1,2,4]triazolo[1,5-a]pyridine (1.78 g, 62%) as an off-white solid with >99.9% purity (HPLC area-%, HPLC method: Onyx monolithic C18 column, 100×4.6 mm; mobile phase, A: water/NCMe (95:5), B: NCMe; flow: 2.0 ml/min; gradient from 95/5 (A/B) to 15/85 (A/B) within 3 min, isocratic 15/85 (A/B) for 2.5 min. Retention time: 3.40 min (2-amino-4-benzyloxypyridine), 3.60 min 7-benzyloxy-2-phenyl-[1,2,4]triazolo[1,5-a]pyridine)).

EI-MS: m/z=302.13 (M+H)⁺.

What is claimed is:

1. A process for the preparation of 2-phenyl-[1,2,4]triazolo[1,5-a]pyridine derivatives of formula I or of a salt thereof

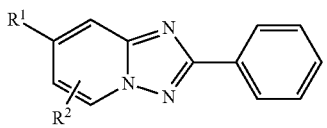

wherein,
$R^1$ stands for hydrogen, a halogen, for an optionally protected hydroxyl group or for an optionally protected amino group and
$R^2$ is hydrogen or a halogen,
which comprises the conversion of a pyridine compound of formula II or of a salt thereof,

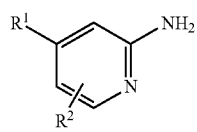

wherein, $R^1$ and $R^2$ are as above,
with benzonitrile in the presence of a Cu-catalyst, a 1,10-phenanthroline derivative and of a mixture $O_2/N_2$, characterized in that no other solvent than the reactant benzonitrile is present in the process.

2. Process of claim 1, characterized in that the reaction temperature is selected between 80° C. and 170° C.

3. Process of claim 2, characterized in that the reaction temperature is selected between 110° C. and 150° C.

4. Process of claim 1, characterized in that the reaction pressure is selected between 1 and 100 bar.

5. Process of claim 1, characterized in that the concentration of the pyridine compound of formula II in benzonitrile is between 2 wt. % and 30 wt. %.

6. Process of claim 5, characterized in that the concentration of the pyridine compound of formula II in benzonitrile is between 5 wt. % and 20 wt. %.

7. Process of claim 1, characterized in that a mixture $O_2/N_2$ with 1 Vol % to 21 Vol % $O_2$ is used.

8. Process of claim 7, characterized in that a mixture $O_2/N_2$ with 3 Vol % to 8 Vol % $O_2$ is used.

9. Process of claim 1, characterized in that the 1,10 phenanthroline derivative is 1,10 phenanthroline monohydrate.

10. Process of claim 1, characterized in that the Cu-catalyst
 is CuBr in case $R^1$ in the pyridine compound of formula II stands for bromine, for an optionally protected hydroxyl group or for an optionally protected amino group,
 is CuBr in case $R^1$ in the pyridine compound of formula II stands for hydrogen and $R^2$ for bromine or hydrogen,
 is CuCl in case $R^1$ in the pyridine compound of formula II stands for chlorine or
 is CuI in case $R^1$ in the pyridine compound of formula II stands for iodine.

11. Process of claim 10, characterized in that the Cu-catalyst is CuBr.

12. Process of claim 1, characterized in that $R^1$ in the pyridine compound of formula II stands for bromine.

13. Process of claim 1, characterized in that $R^2$ is hydrogen.

* * * * *